US012765860B2

(12) United States Patent
Zhao et al.

(10) Patent No.: US 12,765,860 B2
(45) Date of Patent: Oct. 20, 2026

(54) ULTRASOUND DIAGNOSTIC APPARATUS AND FAT FRACTION ESTIMATION METHOD

(71) Applicant: FUJIFILM Corporation, Tokyo (JP)

(72) Inventors: Yu Zhao, Tokyo (JP); Tomohide Nishiyama, Tokyo (JP); Mika Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/007,043

(22) Filed: Dec. 31, 2024

(65) Prior Publication Data

US 2025/0241614 A1 Jul. 31, 2025

(30) Foreign Application Priority Data

Jan. 26, 2024 (JP) ................................ 2024-009937

(51) Int. Cl.

*A61B 8/00* (2006.01)
*A61B 8/08* (2006.01)
*G16H 50/30* (2018.01)

(52) U.S. Cl.

CPC ................ *A61B 8/08* (2013.01); *A61B 8/463* (2013.01); *G16H 50/30* (2018.01)

(58) Field of Classification Search

CPC ........... A61B 8/08; A61B 8/463; A61B 8/469; A61B 8/5207; A61B 8/5223; A61B 8/5246; G16H 50/30; G16H 50/20; G01S 7/52036

See application file for complete search history.

(56) References Cited

U.S. PATENT DOCUMENTS

| | | | | |
|---|---|---|---|---|
| 9,980,677 B1* | 5/2018 | Cho | A61B 5/0035 | |
| 2014/0066767 A1* | 3/2014 | Mammone | A61B 8/0825 | 600/443 |
| 2018/0289323 A1* | 10/2018 | Labyed | A61B 8/463 | |
| 2019/0038220 A1* | 2/2019 | Rubin | A61B 5/4244 | |
| 2020/0205786 A1* | 7/2020 | Labyed | A61B 8/485 | |
| 2023/0104771 A1* | 4/2023 | Labyed | A61B 8/08 | 600/442 |

FOREIGN PATENT DOCUMENTS

| | | |
|---|---|---|
| JP | 2020-000354 A | 1/2020 |
| WO | 2017/068892 A1 | 4/2017 |

OTHER PUBLICATIONS

Hidekatsu Kuroda et al.; "Multivariable Quantitative US Parameters for Assessing Hepatic Steatosis;" Radiology, vol. 309, No. 1, Oct. 2023; pp. 1-9.

* cited by examiner

*Primary Examiner* — Joel Lamprecht
*Assistant Examiner* — James F McDonald, III
(74) *Attorney, Agent, or Firm* — Studebaker Brackett PLLC

(57) ABSTRACT

A two-dimensional region of interest is set within a liver of a subject (S12). A first parameter group including a first attenuation coefficient is calculated based on first reception information obtained from the two-dimensional region of interest (S16). A second parameter group including a second attenuation coefficient is calculated based on second reception information obtained from the two-dimensional region of interest (S20). A parameter set including the first parameter group and the second parameter group is given to a mathematical model to calculate an estimated value of a fat fraction (S22).

7 Claims, 9 Drawing Sheets

ULTRASOUND DIAGNOSTIC APPARATUS AND FAT FRACTION ESTIMATION METHOD

CROSS-REFERENCE TO RELATED APPLICATIONS

This application claims benefit of priority to Japanese Patent Application No. 2024-009937 filed Jan. 26, 2024, the entire contents of which are incorporated herein by reference.

BACKGROUND OF THE INVENTION

1. Field of the Invention

The present disclosure relates to an ultrasound diagnostic apparatus and a fat fraction estimation method, and particularly relates to a technique of estimating a fat fraction of a liver.

2. Description of the Related Art

In order to evaluate properties of a liver tissue, particularly a degree of a fatty liver, it is necessary to measure the fat fraction of the liver.

Some ultrasound diagnostic apparatuses have a function of measuring an attenuation coefficient (attenuation rate) in the liver. In such an ultrasound diagnostic apparatus, ultrasonic waves are transmitted to the liver, and reflected waves from the liver are received. The attenuation coefficient is calculated based on reception information obtained in this manner. The attenuation coefficient is a parameter that changes depending on the properties of the liver tissue. Although there is a certain correlation between the attenuation coefficient and the fat fraction, the attenuation coefficient does not directly represent the fat fraction.

A magnetic resonance imaging (MRI)-proton density fat fraction (PDFF) (hereinafter, simply referred to as a PDFF) of the liver, which is measured by an MRI device, indicates a ratio of an amount of protons contained in water molecules to an amount of protons contained in fat molecules. That is, the PDFF directly represents the fat fraction of the liver. However, the MRI device is an expensive and large-sized device. There is a demand for a technique that allows for more easy measurement of the fat fraction of the liver.

SUMMARY OF THE INVENTION

It is desirable to estimate the fat fraction or calculate a value approximating the PDFF using the ultrasound diagnostic apparatus.

WO2017/0688892A discloses an ultrasound diagnostic apparatus that measures an attenuation coefficient. In the ultrasound diagnostic apparatus, the attenuation coefficient is calculated based on a first reception signal obtained by formation of a first ultrasonic beam and a second reception signal obtained by formation of a second ultrasonic beam. However, WO2017/0688892A does not disclose a technique of estimating a fat fraction, in particular, a technique of estimating a fat fraction based on a plurality of attenuation coefficients.

JP2020-354A also discloses an ultrasound diagnostic apparatus that measures an attenuation coefficient. However, JP2020-354A also does not disclose a technique of estimating a fat fraction.

Hidekatsu Kuroda et al., Multivariable Quantitative US Parameters for Assessing Hepatic Steatosis, Radiology, Volume 309, Number 1, 2023 discloses a relationship between an attenuation coefficient measured by an ultrasound diagnostic apparatus and a PDFF measured by an MRI device. However, Hidekatsu Kuroda et al., Multivariable Quantitative US Parameters for Assessing Hepatic Steatosis, Radiology, Volume 309, Number 1, 2023 also does not disclose a technique of estimating a fat fraction based on a plurality of attenuation coefficients.

An object of the present disclosure is to estimate a fat fraction or calculate a value approximating a PDFF in an ultrasound diagnostic apparatus.

An ultrasound diagnostic apparatus according to the present disclosure comprises: a first calculation unit that calculates a plurality of attenuation coefficients based on a plurality of pieces of reception information acquired from a liver in a subject and having a plurality of different frequency characteristics; and a second calculation unit that calculates an estimated value of a fat fraction based on a parameter set including the plurality of attenuation coefficients.

A fat fraction estimation method according to the present disclosure comprises: a step of calculating a plurality of attenuation coefficients based on a plurality of pieces of reception information acquired from a liver in a subject and having a plurality of different frequency characteristics; and a step of calculating an estimated value of a fat fraction based on a parameter set including the plurality of attenuation coefficients.

According to the present invention, in the ultrasound diagnostic apparatus, the fat fraction can be estimated, or a value approximating the PDFF can be calculated.

DESCRIPTION OF THE PREFERRED EMBODIMENTS

Figure 1:
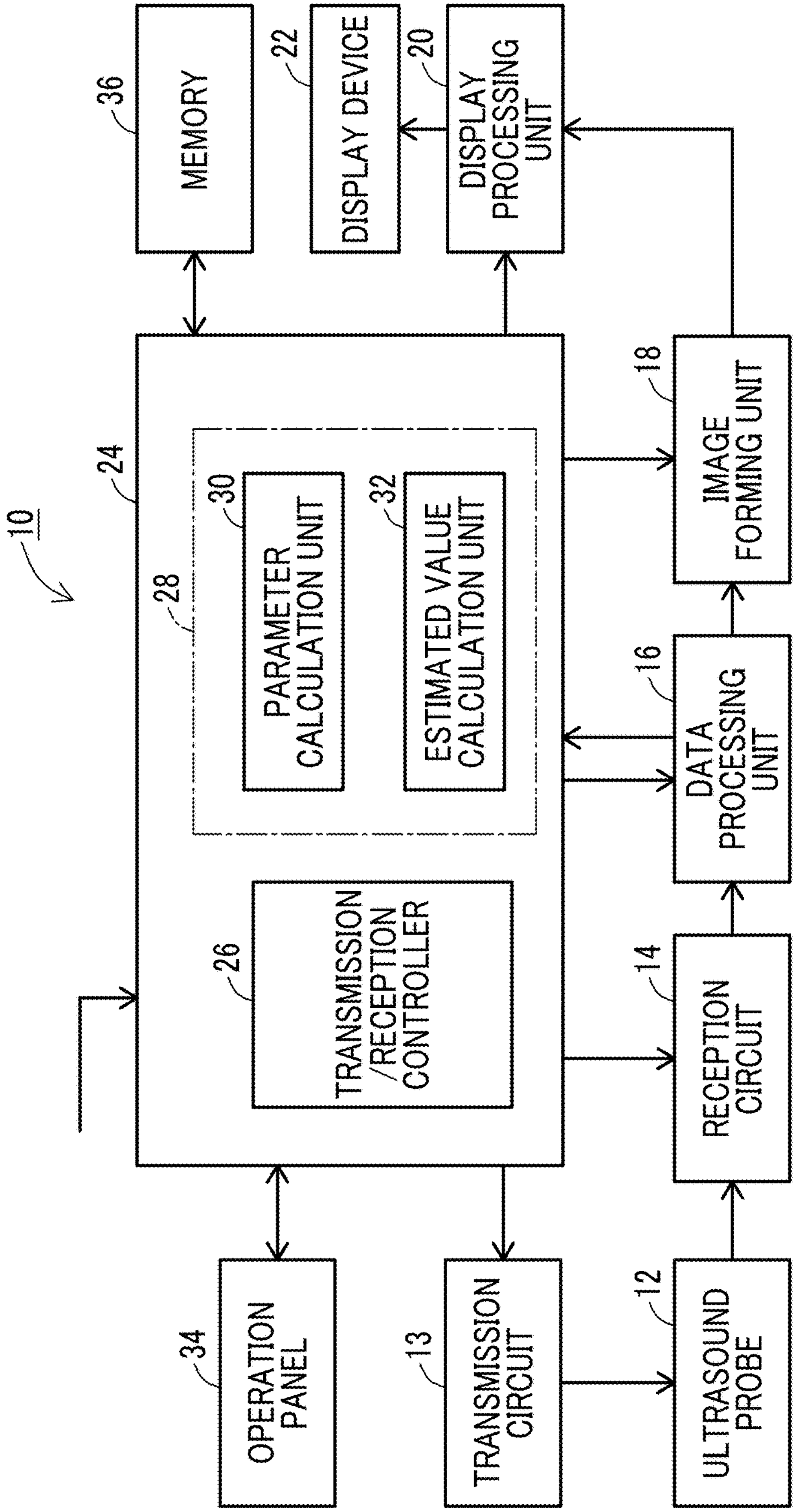
FIG. 1 is a block diagram showing a configuration example of an ultrasound diagnostic apparatus according to an embodiment.

Hereinafter, an embodiment will be described with reference to the drawings.

(1) Summary of Embodiment

An ultrasound diagnostic apparatus according to an embodiment includes a first calculation unit and a second calculation unit. The first calculation unit calculates a plurality of attenuation coefficients based on a plurality of pieces of reception information acquired from a liver in a subject and having a plurality of different frequency characteristics. The second calculation unit calculates an estimated value of a fat fraction based on a parameter set including the plurality of attenuation coefficients.

Acoustic characteristics of a biological tissue depend on a frequency of ultrasonic waves propagating through the biological tissue. The plurality of pieces of reception information all reflect properties of a liver tissue, but have a plurality of different frequency characteristics. The plurality of attenuation coefficients are calculated based on such a plurality of pieces of reception information. By calculating the estimated value of the fat fraction based on the plurality of attenuation coefficients, the reliability of the estimated value can be increased.

In the embodiment, the parameter set includes a plurality of parameters other than the plurality of attenuation coefficients, and the plurality of parameters being calculated from a plurality of reception signals. By using such a parameter set, an estimation accuracy of the fat fraction can be improved. The parameter set may include a parameter other than the parameter obtained by the ultrasound diagnosis. In order to obtain the plurality of reception signals, a plurality of transmission signals having a plurality of different center frequencies may be used, or a plurality of reception filters having a plurality of different frequency characteristics may be used. The frequency characteristic means a frequency band.

In the embodiment, the second calculation unit has a model created such that the estimated value of the fat fraction approximates an MRI-PDFF. The parameter set is given to the model, so that the estimated value of the fat fraction is calculated. The model is, for example, a mathematical model generated by multiple regression analysis or an AI model generated through a machine learning process. The mathematical model means one or a plurality of calculation formulae.

In the embodiment, the plurality of pieces of reception information include first reception information having a first frequency characteristic and second reception information having a second frequency characteristic. The plurality of attenuation coefficients include a first attenuation coefficient calculated based on the first reception information and a second attenuation coefficient calculated based on the second reception information. The plurality of pieces of reception information may be composed of three or more pieces of reception information, and the plurality of attenuation coefficients may be composed of three or more attenuation coefficients.

The ultrasound diagnostic apparatus according to the embodiment includes an ultrasound probe. The ultrasound probe acquires the first reception information by transmitting a first ultrasonic wave having a first center frequency into the subject. In addition, the ultrasound probe acquires the second reception information by transmitting a second ultrasonic wave having a second center frequency different from the first center frequency into the subject.

In the embodiment, transmission/reception for forming a tomographic image, transmission/reception for acquiring the first reception information, and transmission/reception for acquiring the second reception information are executed. All or a part of these types of transmission/reception may be integrated.

The ultrasound diagnostic apparatus according to the embodiment includes a generator. The generator generates first reference information to be compared with the first reception information and second reference information to be compared with the second reception information. The first calculation unit calculates the first attenuation coefficient based on the first reception information and the first reference information. In addition, the first calculation unit calculates the second attenuation coefficient based on the second reception information and the second reference information.

In the embodiment, the first reference information and the second reference information are each defined by a predetermined calculation formula. In this case, an information generator is composed of a calculating device. The first reference information and the second reference information may each be configured as a predetermined numerical value sequence. In that case, the generator may be composed of a memory.

In the embodiment, the first reception information and the second reception information are each information acquired from a two-dimensional region within the subject. The first calculation unit calculates a first attenuation matrix based on the first reception information and the first reference information, and calculates a first parameter group including the first attenuation coefficient, a first attenuation average, and a first attenuation variation based on the first attenuation matrix. In addition, the first calculation unit calculates a second attenuation matrix based on the second reception information and the second reference information, and calculates a second parameter group including the second attenuation coefficient, a second attenuation average, and a second attenuation variation based on the second attenuation matrix. The parameter set includes the first parameter group and the second parameter group.

The first attenuation matrix and the second attenuation matrix are each a matrix consisting of a plurality of elements corresponding to a plurality of two-dimensional coordinates. For example, each element is a relative attenuation (relative attenuation amount). Each element may be an absolute attenuation (absolute attenuation amount). The first attenuation average and the second attenuation average are each a two-dimensional average of the relative attenuation (or the absolute attenuation). The first attenuation average and the second attenuation average may each be a two-dimensional average of the attenuation coefficients. Meanwhile, the first attenuation variation and the second attenuation variation are each a two-dimensional variation of the relative attenuation (or the absolute attenuation). Specifically, the variation is a standard deviation, a variance, or the like. The first attenuation variation and the second attenuation variation may each be a two-dimensional variation of the attenuation coefficients.

In the embodiment, the two-dimensional region corresponds to a plurality of reception beams aligned in an electronic scanning direction. The first calculation unit calculates the first attenuation coefficient based on a specific attenuation sequence selected from the first attenuation matrix, and calculates the first attenuation average and the first attenuation variation based on a plurality of attenuation sequences in the first attenuation matrix. In addition, the first calculation unit calculates the second attenuation coefficient based on a specific attenuation sequence selected from the second attenuation matrix, and calculates the second attenuation average and the second attenuation variation based on a plurality of attenuation sequences in the second attenuation matrix.

In the embodiment, the parameter set further includes one or a plurality of parameters acquired from the subject by an examination other than an ultrasound examination. Examples of such one or a plurality of parameters include a height, a weight, a BMI, and a blood test value of the subject. The parameter set may include a tomographic image analysis result.

The ultrasound diagnostic apparatus according to the embodiment includes a forming device and a display device. The forming device forms an ultrasound image based on reception information different from the plurality of pieces of reception information. The display device displays the ultrasound image, at least one of the plurality of attenuation coefficients, and the estimated value of the fat fraction.

A fat fraction estimation method according to the embodiment includes a first step and a second step. In the first step, a plurality of attenuation coefficients are calculated based on a plurality of pieces of reception information acquired from a liver in a subject and having a plurality of different frequency characteristics. In the second step, an estimated value of a fat fraction is calculated based on a parameter set including the plurality of attenuation coefficients.

The above-described fat fraction estimation method can be realized as a function of a program. In this case, the program is installed in an information processing apparatus via a network or a portable memory. The information processing apparatus is an ultrasound diagnostic apparatus, a computer, or the like. The information processing apparatus includes a non-transitory storage medium that stores the program.

(2) Details of Embodiment

FIG. 1 shows an ultrasound diagnostic apparatus 10 according to the embodiment. The ultrasound diagnostic apparatus 10 is a medical apparatus that is provided in a medical institution such as a hospital and that is used for an ultrasound examination of a subject (living body). The ultrasound diagnostic apparatus 10 according to the embodiment has an operation mode of estimating a fat fraction of a liver (hereinafter, referred to as a fat fraction estimation mode), in addition to a B-mode in which a tomographic image is displayed.

In FIG. 1, an ultrasound probe 12 is a portable device that transmits and receives ultrasonic waves to acquire reception information. The ultrasound probe 12 has a transducer array consisting of a plurality of transducers arranged in a linear or curved shape. The transducer array forms an ultrasonic beam. Electronic scanning with the ultrasonic beam is performed. As an electronic scanning method, an electronic linear scanning method, an electronic sector scanning method, or the like is known. A two-dimensional transducer array may be provided in the ultrasound probe 12.

A transmission circuit 13 is an electronic circuit that functions as a transmission beam former. During the transmission, the transmission circuit 13 supplies a plurality of transmission signals to the transducer array in parallel. As a result, a transmission beam is formed by the transducer array.

A reception circuit 14 is an electronic circuit that functions as a reception beam former. During the reception, in a case in which a reflected wave from the living body is received by the transducer array, a plurality of reception signals are output in parallel from the transducer array. The reception circuit 14 applies phase addition to the plurality of reception signals, thereby generating reception beam data. The reception circuit 14 includes a plurality of amplifiers, a plurality of A/D converters, a phase adjustment addition circuit, and the like.

In a case in which the B-mode is executed, the electronic scanning with the ultrasonic beam is performed over the entire electronic scanning range. As a result, reception frame data is obtained. The reception frame data is composed of a plurality of reception beam data aligned in the electronic scanning direction. Each reception beam data is composed of a plurality of echo data aligned in a depth direction. The reception frame data is B-mode reception information. With the repetition of the electronic scanning with the ultrasonic beam, a plurality of reception frame data are sequentially output from the reception circuit 14.

In a case in which the fat fraction estimation mode is executed, first transmission/reception and second transmission/reception, which are different from the transmission/reception for the B-mode, are sequentially executed. Specifically, the first transmission/reception and the second transmission/reception are sequentially executed for a two-dimensional region of interest set in the liver, which is an examination target.

In the first transmission/reception, a first ultrasonic wave having a first center frequency is transmitted into the subject, and a first reflected wave from within the subject is received, thereby acquiring the first reception information. The first reception information consists of a plurality of first reception beam data (first reception beam data set) corresponding to a plurality of first reception beams passing through a region of interest. More specifically, the first reception beam data set is composed of a plurality of echo data corresponding to a plurality of observation points (sampling points) that spread two-dimensionally in the region of interest.

In the second transmission/reception, a second ultrasonic wave having a second center frequency different from the first center frequency is transmitted into the subject, and a second reflected wave from within the subject is received, thereby acquiring the second reception information. The second reception information consists of a plurality of second reception beam data (second reception beam data set) corresponding to a plurality of second reception beams passing through a region of interest. More specifically, the second reception beam data set is composed of a plurality of echo data corresponding to a plurality of observation points (sampling points) that spread two-dimensionally in the region of interest. The first center frequency is, for example, 1.5 MHz, 2 MHZ, or 2.5 MHz, and the second center frequency is, for example, 3 MHz, 4 MHZ, or 5 MHz.

A data processing unit 16 is an electronic circuit that applies necessary processing to each reception beam data. The data processing unit 16 includes an envelope detection circuit, a smoothing circuit, a logarithmic compression circuit, and the like. In a case in which the B-mode is executed, the plurality of reception frame data are sequentially sent from the data processing unit 16 to an image forming unit 18. In a case in which the fat fraction estimation mode is executed, the first reception beam data set and the second reception beam data set are sequentially sent from the data processing unit 16 to an information processing unit 24.

The image forming unit 18 sequentially generates a plurality of tomographic image data based on the plurality of reception frame data. The image forming unit 18 includes a digital scan converter (DSC) having a coordinate transformation function, a pixel interpolation function, and the like.

The plurality of tomographic image data are sent to a display device 22 via a display processing unit 20. A plurality of tomographic images are displayed as a moving image on the display device 22. In a case in which a freeze operation is performed, a tomographic image corresponding to a specific time phase is displayed as a still image. The display device 22 is composed of an organic EL display or the like. In a case in which the fat fraction estimation mode is executed, the display device 22 displays the attenuation coefficient, the estimated value of the fat fraction (estimated PDFE value), and the like in addition to the tomographic image as the still image.

The information processing unit 24 is composed of a CPU executing a program. The information processing unit 24 has a function of controlling an operation of each element constituting the ultrasound diagnostic apparatus 10. In FIG. 1, a plurality of main functions exhibited by the information processing unit 24 are represented by a plurality of blocks. The information processing unit 24 includes a transmission/reception controller 26 and a calculation module 28. The calculation module 28 includes a parameter calculation unit (first calculation unit) 30 and an estimated value calculation unit (second calculation unit) 32.

The transmission/reception controller 26 controls the transmission and reception of the ultrasonic waves. Specifically, the transmission/reception controller 26 controls the operations of the transmission circuit 13 and the reception circuit 14. As will be described below, the parameter calculation unit 30 has a function of calculating the first parameter group based on the first reception information and a function of calculating the second parameter group based on the second reception information. The estimated value calculation unit 32 has a function of calculating the estimated value of the fat fraction based on the parameter set including the first parameter group and the second parameter group.

An operation panel 34 is an input device, and includes a plurality of switches, a plurality of buttons, a trackball, and the like. An examiner selects the operation mode and sets the region of interest through the operation panel 34.

A memory 36 is composed of, for example, a semiconductor memory. The memory 36 stores information and a program required for operating the ultrasound diagnostic apparatus 10. The stored information includes information for defining the first reference information and the second reference information used in the fat fraction estimation mode. One or a plurality of examination value data from an external device are input to the information processing unit 24. The examination value data includes, for example, BMI data and blood test data. Each component shown in FIG. 1 is configured of an electronic circuit, a processor, a device, and the like.

Figure 2:
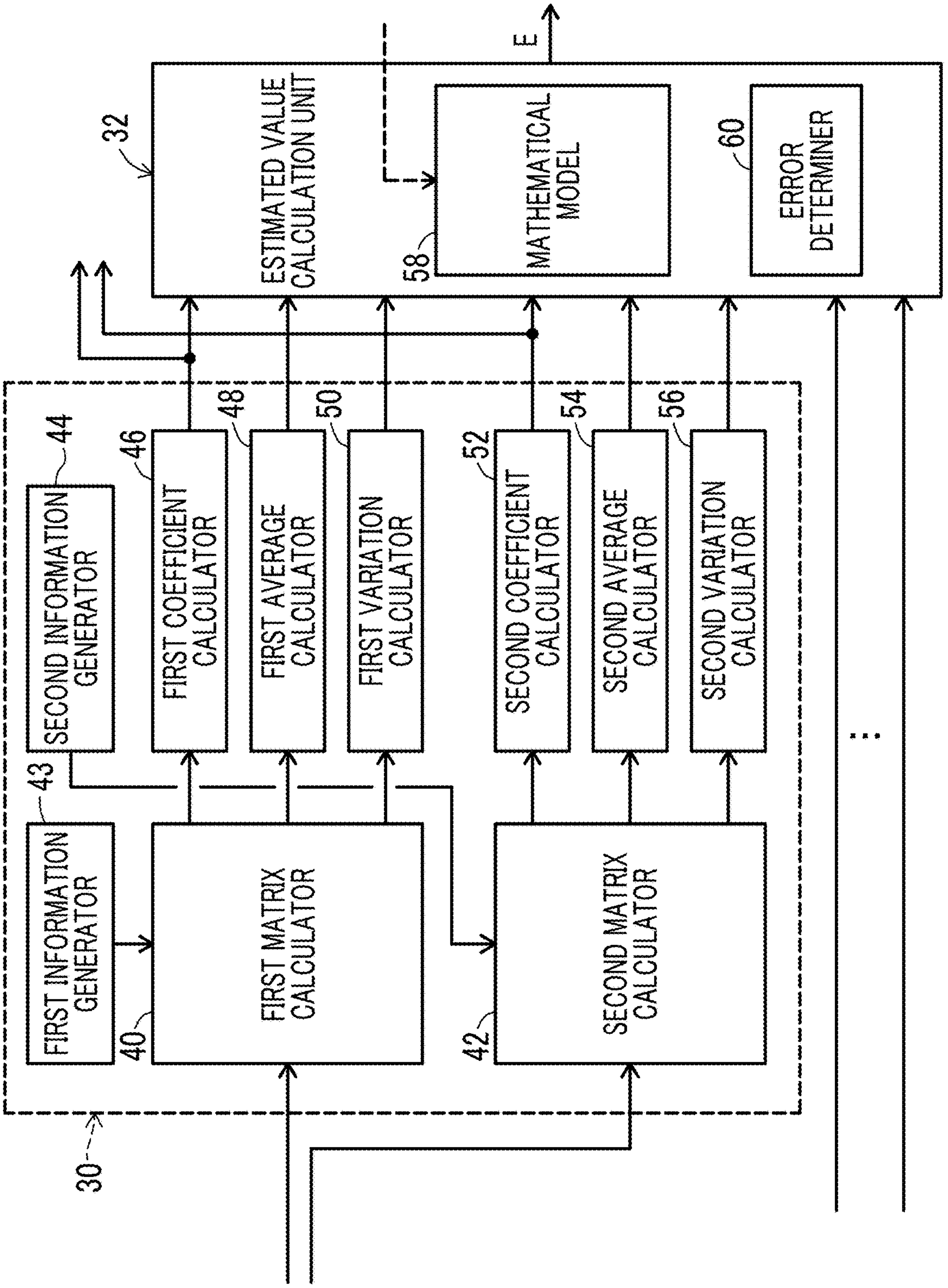
FIG. 2 is a block diagram showing a configuration example of a calculation module shown in FIG. 1.

FIG. 2 shows configuration examples of the parameter calculation unit 30 and the estimated value calculation unit 32 shown in FIG. 1. These function in the fat fraction estimation mode.

The parameter calculation unit 30 includes a first matrix calculator 40, a second matrix calculator 42, a first information generator 43, a second information generator 44, a first coefficient calculator 46, a first average calculator 48, a first variation calculator 50, a second coefficient calculator 52, a second average calculator 54, and a second variation calculator 56.

The first matrix calculator 40 calculates a first attenuation matrix based on the first reception information. The first attenuation matrix may also be referred to as a first attenuation amount matrix. Specifically, the first matrix calculator 40 calculates a first attenuation matrix as a two-dimensional matrix based on a two-dimensional first reception intensity matrix acquired from within the region of interest and an one-dimensional first reference intensity sequence output from the first information generator 43.

The second matrix calculator 42 calculates a second attenuation matrix based on the second reception information. The second attenuation matrix may also be referred to as a second attenuation amount matrix. Specifically, the second matrix calculator 42 calculates a second attenuation matrix as a two-dimensional matrix based on a two-dimensional second reception intensity matrix acquired from within the region of interest and an one-dimensional second reference intensity sequence output from the second information generator 44.

The first information generator 43 generates the first reference intensity sequence according to a first reference intensity function. The second information generator 44 generates the second reference intensity sequence according to a second reference intensity function. The calculated or measured first reference intensity sequence and second reference intensity sequence may be stored in a memory (see FIG. 1) in advance.

The first coefficient calculator 46 calculates a first attenuation coefficient (first attenuation rate) based on a specific first attenuation sequence selected from the first attenuation matrix. In the embodiment, the specific first attenuation sequence corresponds to the reception beam passing through the center of the region of interest.

The first average calculator 48 calculates a first attenuation average based on a plurality of first attenuation sequences constituting the first attenuation matrix. The first attenuation average may also be referred to as a first attenuation amount average. The first attenuation average may be calculated based on a part of the first attenuation matrix.

The first variation calculator 50 calculates a first attenuation variation based on the plurality of first attenuation sequences constituting the first attenuation matrix. The first attenuation variation may also be referred to as a first attenuation amount variation. The first attenuation variation may be calculated based on a part of the first attenuation matrix. Specifically, the first attenuation variation is a standard deviation (SD). As the first attenuation variation, a variance or the like may be calculated.

The second coefficient calculator 52 calculates a second attenuation coefficient (second attenuation rate) based on a specific second attenuation sequence selected from the second attenuation matrix. In the embodiment, the specific second attenuation sequence corresponds to the reception beam passing through the center of the region of interest.

The second average calculator 54 calculates a second attenuation average based on a plurality of second attenuation sequences constituting the second attenuation matrix. The second attenuation average may also be referred to as a second attenuation amount average. The second attenuation average may be calculated based on a part of the second attenuation matrix.

The second variation calculator 56 calculates a second attenuation variation based on the plurality of second attenuation sequences constituting the second attenuation matrix. The second attenuation variation may also be referred to as a second attenuation amount variation. The second attenuation variation may be calculated based on a part of the second attenuation matrix. Specifically, the second attenuation variation is a standard deviation (SD). As the second attenuation variation, a variance or the like may be calculated.

The first attenuation coefficient, the first attenuation average, and the first attenuation variation constitute a first parameter group. The second attenuation coefficient, the second attenuation average, and the second attenuation variation constitute a second parameter group. The parameter set includes the first parameter group and the second parameter group. In the embodiment, the parameter set further includes an examination value acquired from the subject by an examination other than the ultrasound examination. Specifically, the parameter set further includes a body mass index (BMI). The parameter set may include an examination value instead of the BMI, or may include other examination values with the BMI.

The estimated value calculation unit 32 has a mathematical model 58. The mathematical model 58 consists of one or a plurality of mathematical expressions for calculating the estimated value of the fat fraction based on the parameter set. A model that has been subjected to machine learning may be used instead of the mathematical model 58. The model that has been subjected to machine learning is composed of a neural network or the like, receives the parameter set as an input, and outputs the estimated value of the fat fraction.

The estimated value calculation unit 32 according to the embodiment includes an error determiner 60. The error determiner 60 determines an error based on the first reception information and/or the second reception information. For example, in a case in which a blood vessel, an artifact, or the like is included in the region of interest, the error determiner 60 determines an error. An error may be determined based on one or both of the first attenuation variation and the second attenuation variation. In a case in which the error is determined, error information is provided to a user. Thereafter, the first transmission/reception and the second transmission/reception are executed again after a position of the region of interest is changed by the user.

Figure 3:
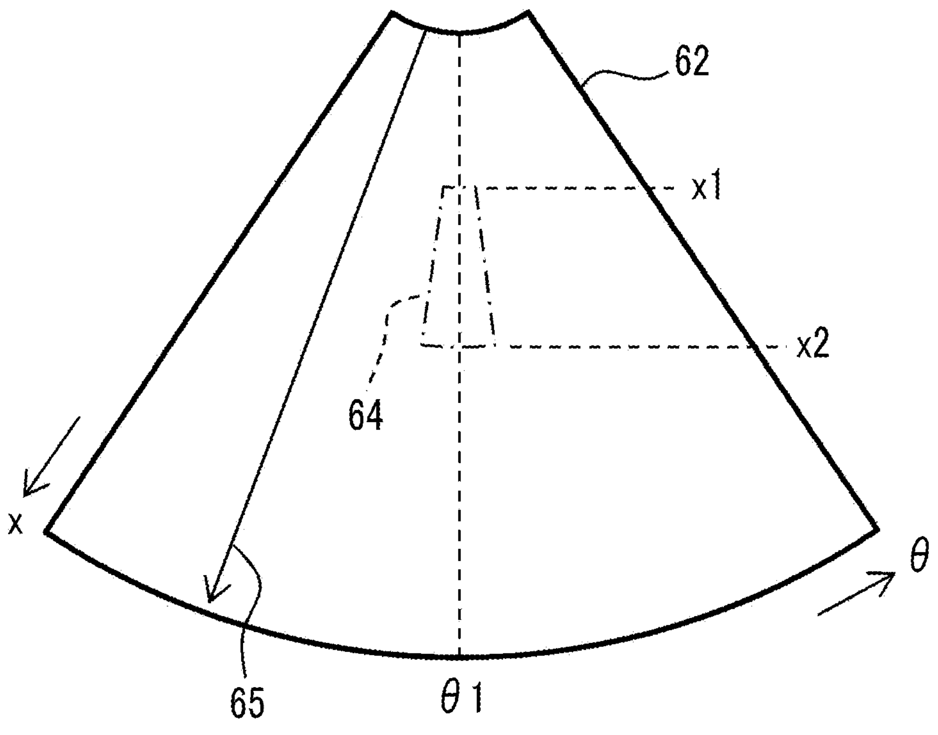
FIG. 3 is a diagram showing a region of interest.

FIG. 3 shows a region of interest 64 set on a beam scanning plane 62. In FIG. 3, an x direction is a depth direction, and a θ direction is an electronic scanning direction. The beam scanning plane 62 is formed by performing electronic scanning with an ultrasonic beam 65.

The region of interest 64 is a two-dimensional region. Specifically, the region of interest 64 extends from a depth x1 to a depth x2 in the depth direction. The region of interest 64 corresponds to an arrangement of N reception beams in the electronic scanning direction. N is, for example, 9, 11, or 13. In the embodiment, the depth x1 and the depth x2 are each a fixed value. The depths x1 and x2 may be designated by the user. An azimuth θ1 is an azimuth corresponding to the center of the region of interest 64. The user can change the azimuth θ1. For example, the region of interest 64 is set such that a large blood vessel does not enter the region of interest 64. The region of interest 64 is actually designated on a tomographic image.

Figure 4:
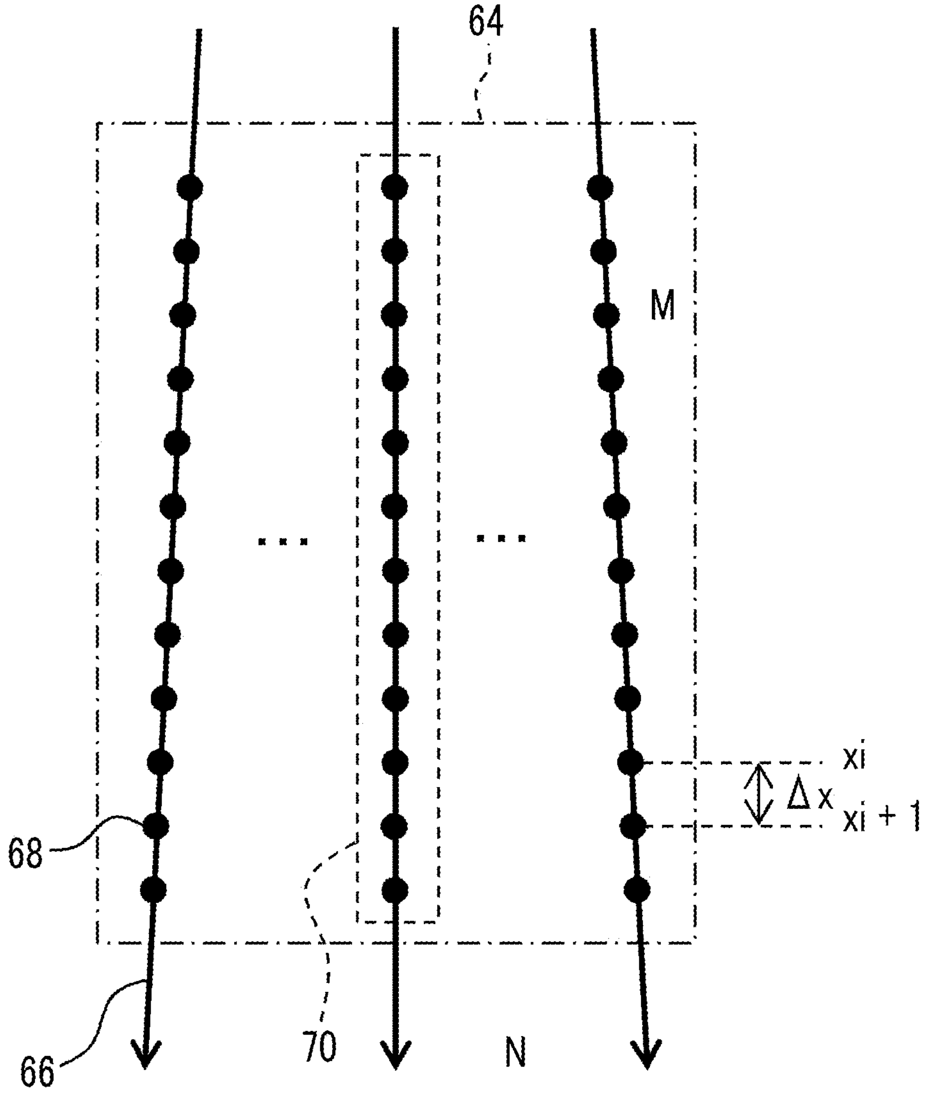
FIG. 4 is a diagram showing a reception intensity matrix.

FIG. 4 shows N reception beams 66 passing through the region of interest 64. Each reception beam 66 includes M reception intensities (amplitude values) 68 aligned in the depth direction. The first reception intensity matrix obtained by the first transmission/reception consists of M×N reception intensities aligned in the depth direction and the electronic scanning direction. Similarly, the second reception intensity matrix obtained by the second transmission/reception consists of M×N reception intensities aligned in the depth direction and the electronic scanning direction. Reference numeral 70 indicates a reception intensity sequence located at the center of the region of interest. In the depth direction, an observation point pitch is denoted by Δx.

Next, the fat fraction estimation method according to the embodiment will be described. First, calculation of an attenuation matrix, an attenuation coefficient, an attenuation average, and an attenuation variation will be described, and then calculation of an estimated value approximating the PDFF will be described. The entity of each attenuation constituting the attenuation matrix is an attenuation amount.

Theoretically, a two-dimensional attenuation matrix $A_a$ is defined by Expression (1) based on a two-dimensional reception intensity matrix P(x).

$$A_a = -\frac{1}{2f}\left(20\log_{10}(P(x))\right) \tag{1}$$

Here, f is a frequency (typically, a center frequency) of the ultrasonic wave, and x is a depth (coordinate in the depth direction). The reception intensity matrix P(x) consists of a plurality of reception intensities obtained from a plurality of observation points constituting the two-dimensional region of interest.

In Expression (1), each attenuation constituting the attenuation matrix $A_a$ corresponds to an absolute attenuation. The absolute attenuation greatly changes depending on operation conditions of the ultrasound diagnostic apparatus and the like. Therefore, in general, an attenuation sequence $A_r$ is obtained by comparing the reception intensity matrix P(x) with a reference intensity sequence (reference signal) $P_{ref}(x)$ according to Expression (2). A common reference intensity sequence $P_{ref}(x)$ is applied to a plurality of reception intensity sequences aligned in the electronic scanning direction.

$$A_r = -\frac{1}{2f}\left(20\log_{10}\left(\frac{P(x)}{P_{ref}(x)}\right)\right) \tag{2}$$

The attenuation matrix $A_r$ is composed of a plurality of attenuations aligned in the depth direction and the electronic scanning direction. Each attenuation is a relative attenuation. The final attenuation (absolute attenuation) is obtained by adding a known attenuation corresponding to the reference intensity sequence $P_{ref}(x)$ to each attenuation.

The reference intensity sequence $P_{ref}(x)$ is defined by, for example, Expression (3). The following γ is a coefficient.

$$P_{ref}(x) = 10^{-\gamma x} \tag{3}$$

The reference intensity sequence $P_{ref}(x)$ may be defined by another function. The reference intensity sequence may be given as a numerical value sequence.

An attenuation coefficient sequence $\alpha_r$ is calculated according to Expression (4).

$$\alpha_r = \frac{1}{M}\sum_{i=1}^{M}\frac{\left(A_{rc}(x_i) - A_{rc}(x_{i-1})\right)}{\Delta x} \tag{4}$$

Here, i indicates a depth number. $A_{re}(x_i)$ represents a central attenuation sequence in the attenuation matrix. Δx is defined by Expression (5).

$$\Delta x = x_i - x_{i-1} \tag{5}$$

Each attenuation constituting the attenuation coefficient sequence $\alpha_r$ is a relative attenuation coefficient. According to Expression (6), the attenuation coefficient (absolute attenuation coefficient) α at each depth is calculated.

$$\alpha = k1 * (\alpha_r + k2) + k3 \tag{6}$$

Here, k2 is a known attenuation coefficient corresponding to the reference intensity sequence $P_{ref}(x)$. k1 and k3 are coefficients for adjustment.

Meanwhile, an attenuation average μ is calculated according to Expression (7).

$$\mu = \frac{1}{M \times N} \sum_{i=1}^{M} \sum_{j=1}^{N} A_{ri,j} \tag{7}$$

Here, M represents the number of observation points in the depth direction in the region of interest. N represents the number of observation points in the electronic scanning direction in the region of interest. i indicates a coordinate in the depth direction, and j indicates a coordinate in the electronic scanning direction. $A_{r\ i,j}$ indicates an attenuation corresponding to an observation point (i,j). As the attenuation average μ, an average of the attenuation coefficients may be calculated.

As the attenuation variation, an attenuation standard deviation (attenuation SD) σ is calculated according to Expression (8).

$$\sigma = \sqrt{\frac{1}{M \times N} \sum_{i=1}^{M} \sum_{j=1}^{N} (A_{ri,j} - \mu)^2} \tag{8}$$

The variance may be calculated instead of the attenuation SDσ, or another index representing the variation in attenuation may be calculated.

In the embodiment, prior to calculation of an estimated value E of the fat fraction, an intermediate value Y is calculated according to Expression (9).

$$Y = a*\alpha_1 + b*\mu_1 + c*\sigma_1 + d*\alpha_2 + e*\mu_2 + f*\sigma_2 + g*BMI + h \tag{9}$$

Here, a, b, c, d, e, f, g, and h are coefficients, which are decided in advance by multiple regression analysis described below. Among these coefficients, h corresponds to an offset. $\alpha_1$ is a first attenuation coefficient obtained from the first reception information, $\mu_1$ is a first attenuation average obtained from the first reception information, and $\sigma_1$ is a first attenuation standard deviation obtained from the first reception information. $\alpha_2$ is a second attenuation coefficient obtained from the second reception information, $\mu_2$ is a second attenuation average obtained from the second reception information, and $\sigma_2$ is a second attenuation standard deviation obtained from the second reception information. BMI is a BMI value of the subject.

The estimated value E is calculated from the intermediate value Y according to Expression (10).

$$E = B^{(Y-C)/A} \tag{10}$$

Here, B, C, and A are coefficients.

There is a nonlinear relationship (specifically, a logarithmic relationship) between the intermediate value Y and the PDFF, which is represented by Expression (11).

$$Y = A * \log_B(PDFF) + C \tag{11}$$

In the embodiment, the intermediate value Y is obtained in order to respond to the above-described nonlinear relationship on the premise of multiple regression analysis. The estimated value E may be directly calculated from a combination of $\alpha_1$, $\mu_1$, $\sigma_1$, $\alpha_2$, $\mu_2$, $\sigma_2$, and BMI without going through the calculation of the intermediate value Y. In this case, an estimation model that has been subjected to machine learning may be used.

Figure 5:
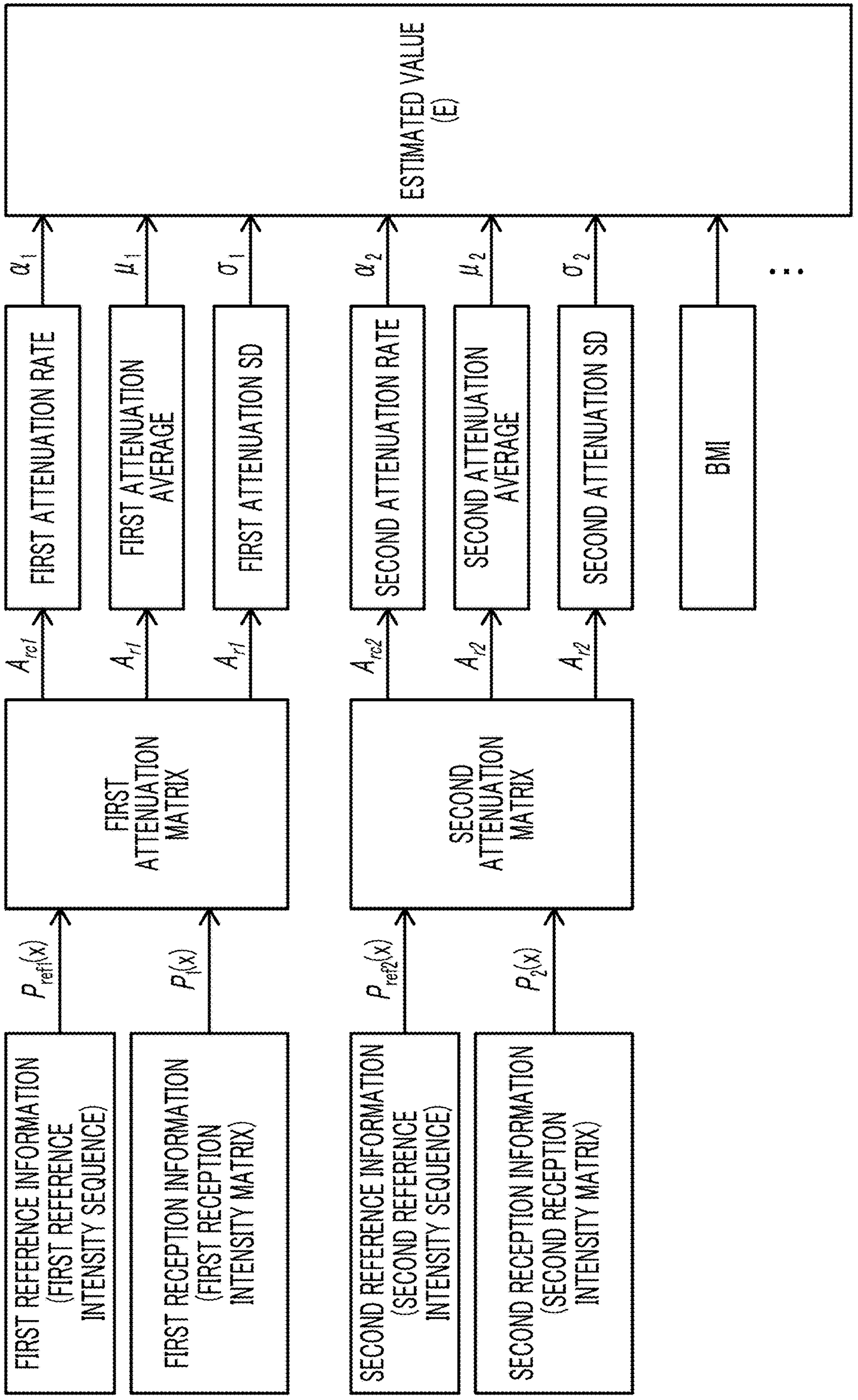
FIG. 5 is a diagram showing a fat fraction estimation method.

FIG. 5 shows an estimated value calculation process. The entity of the first reception information is a first reception intensity matrix $P_1(x)$, and the entity of the second reception information is a second reception intensity matrix $P_2(x)$. The entity of the first reference information is a first reference intensity sequence $P_{ref1}(x)$, and the entity of the second reference information is a second reference intensity sequence $P_{ref2}(x)$.

A first attenuation matrix $A_{r1}$ is calculated based on the first reception intensity matrix $P_1(x)$ and the first reference intensity sequence $P_{ref1}(x)$. A second attenuation matrix $A_{r2}$ is calculated based on the second reception intensity matrix $P_2(x)$ and the second reference intensity sequence $P_{ref2}(x)$. A common first reference intensity sequence $P_{ref1}(x)$ is applied to the plurality of first reception intensity sequences constituting the first reception intensity matrix $P_1(x)$. Similarly, a common second reference intensity sequence $P_{ref2}(x)$ is applied to the plurality of second reception intensity sequences constituting the second reception intensity matrix $P_2(x)$.

The first attenuation coefficient $\alpha_1$ is calculated by comparing a central attenuation sequence $A_{rc1}$ in the first attenuation matrix $A_{r1}$ with the first reference intensity sequence $P_{ref1}(x)$. The first attenuation average $\mu_1$ and the first attenuation SD $\sigma_1$ are calculated based on the first attenuation matrix $A_{r1}$. The first attenuation coefficient $\alpha_1$, the first attenuation average $\mu_1$, and the first standard deviation $\sigma_1$ constitute a first parameter group.

The second attenuation coefficient $\alpha_2$ is calculated by comparing a central attenuation sequence $A_{re2}$ in the second attenuation matrix $A_{r2}$ with the second reference intensity sequence $P_{ref2}(x)$. The second attenuation average $\mu_2$ and the second attenuation SD $\sigma_2$ are calculated based on the second attenuation matrix $A_{r2}$. The second attenuation coefficient $\alpha_2$, the second attenuation average $\mu_2$, and the second attenuation SD $\sigma_2$ constitute a second parameter group. The parameter set includes the first parameter group, the second parameter group, and the BMI.

The estimated value E of the fat fraction is calculated based on the parameter set. Since the estimated value E is based on the PDFF obtained by the actual measurement of a large number of subjects as will be described below, the estimated value E is a value approximating the PDFF.

Figure 6:
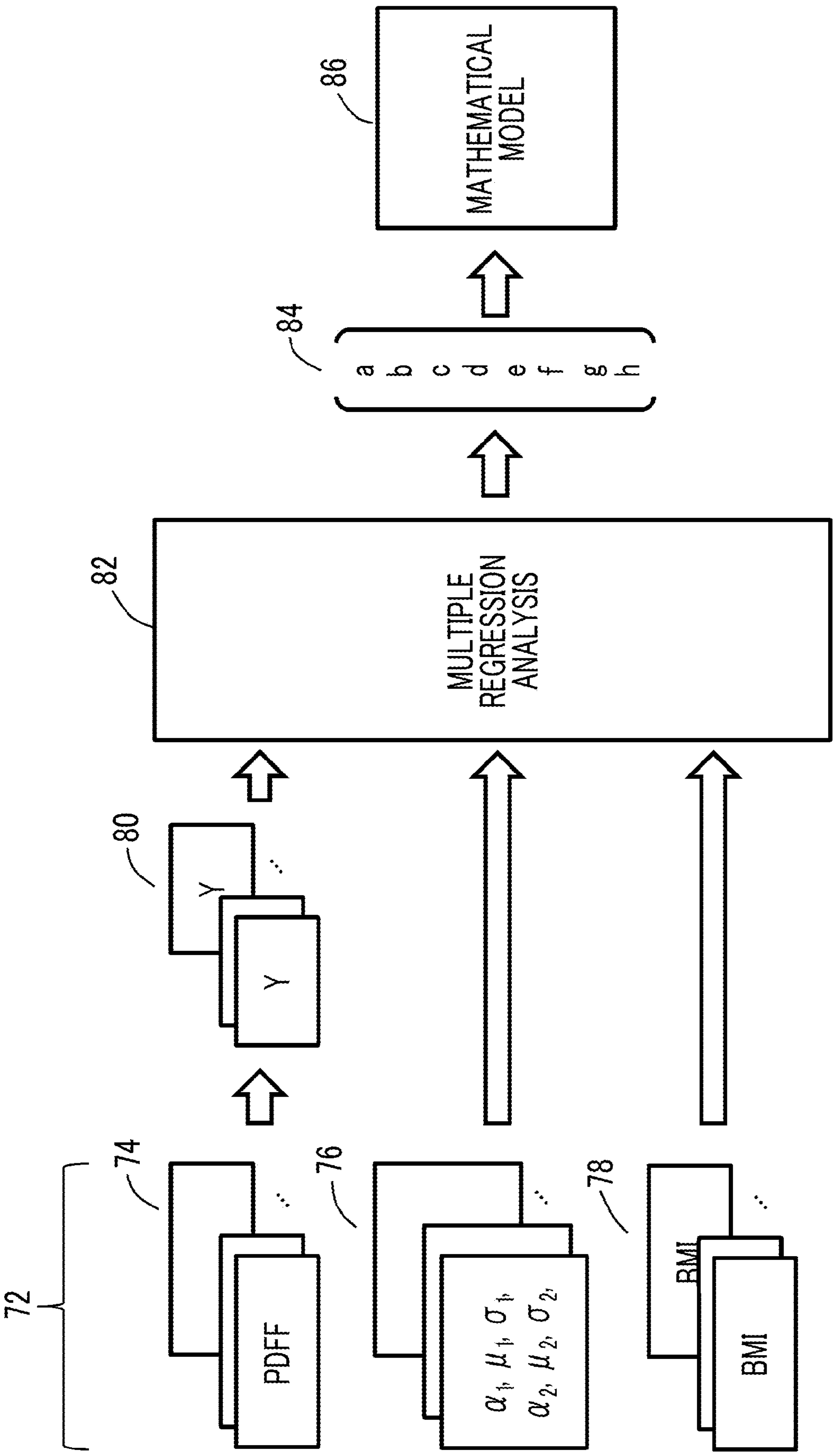
FIG. 6 is a diagram showing a mathematical model creation method.

FIG. 6 shows a method of generating a mathematical model. A PDFF group 74, a parameter group 76, and a BMI group 78 are acquired by executing the MRI examination, the ultrasound examination, and other examinations on a large number of subjects (see reference numeral 72). The PDFF group 74 is converted into an intermediate value group 80 based on Expression (11). The coefficients A, B, and C in Expression (11) are decided in advance. The coefficients a to h and the coefficients A, B, and C may be simultaneously decided by an optimal solution search method or the like.

A coefficient set (a to h) 84 is decided by multiple regression analysis 82 based on the intermediate value group 80, the parameter group 76, and the BMI group 78. As a result, Expression (9) is defined as a mathematical model 86. An estimation model may be generated by machine learning using the PDFF group 74, the parameter group 76, and the BMI group 78.

Figure 7:
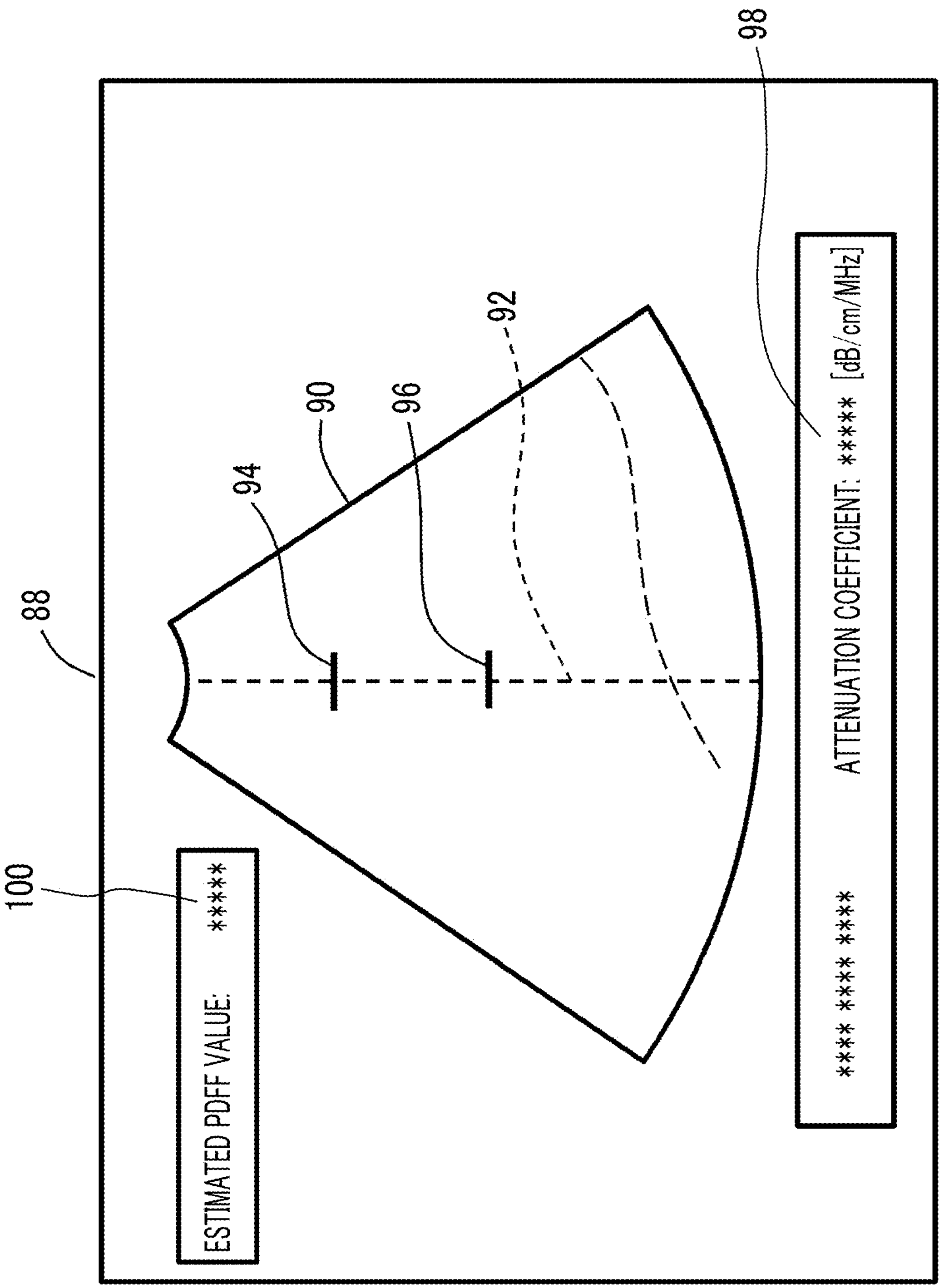
FIG. 7 is a diagram showing a display example.

FIG. 7 shows a display example. A tomographic image 90 as the ultrasound image is displayed on a screen 88 of the display device. The tomographic image 90 shows a cross section of the liver of the subject. The tomographic image 90 includes a first marker 94 and a second marker 96 indicating both ends of the region of interest in the depth direction. A line 92 represents a center line of the region of interest.

As a result of executing the fat fraction estimation mode, an attenuation coefficient 98 is displayed as a numerical value on the screen 88, and an estimated value 100 is displayed as a numerical value. The attenuation coefficient 98 is the first attenuation coefficient or the second attenuation coefficient. An average value thereof may be displayed as the attenuation coefficient 98. In a case in which an error is determined, error information is displayed on the screen 88.

Figure 8:
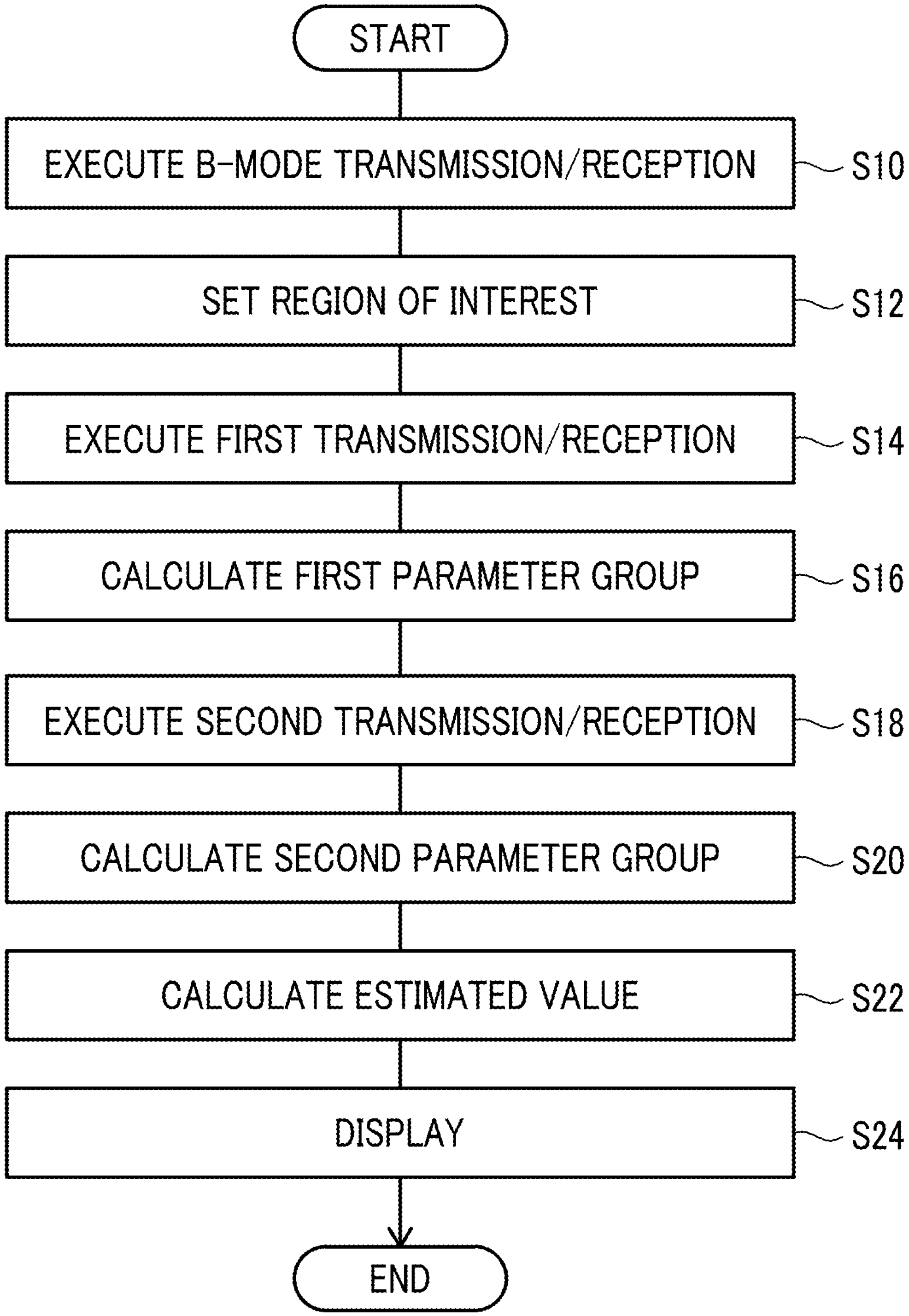
FIG. 8 is a flowchart showing an operation of the ultrasound diagnostic apparatus shown in FIG. 1.

Next, an operation example of the ultrasound diagnostic apparatus shown in FIG. 1 will be described with reference to FIG. 8. In S10, the B-mode transmission/reception is executed. As a result, a tomographic image showing the liver is displayed on the display device. In S12, the region of interest is set on the tomographic image. Then, the execution of the fat fraction estimation mode is started.

In S14, the first transmission/reception is executed. Specifically, the first ultrasonic wave having the first center frequency is transmitted from the ultrasound probe to the region of interest. Then, the first reflected wave from the region of interest is received by the ultrasound probe. As a result, the first reception information is acquired. In S16, the first parameter group including the first attenuation coefficient is calculated based on the first reception information.

In S18, the second transmission/reception is executed. Specifically, the second ultrasonic wave having the second center frequency is transmitted from the ultrasound probe to the region of interest. Then, the second reflected wave from the region of interest is received by the ultrasound probe. As a result, the second reception information is acquired. In S20, the second parameter group including the second attenuation coefficient is calculated based on the second reception information. In practice, S18 is executed immediately after the end of S14, and S20 is executed immediately after the end of S16.

In S22, the estimated value of the fat fraction is calculated based on the parameter set including the first parameter group and the second parameter group. In S24, the estimated value is displayed together with the attenuation coefficient. In this case, the entire parameter set may be displayed.

Figure 9:
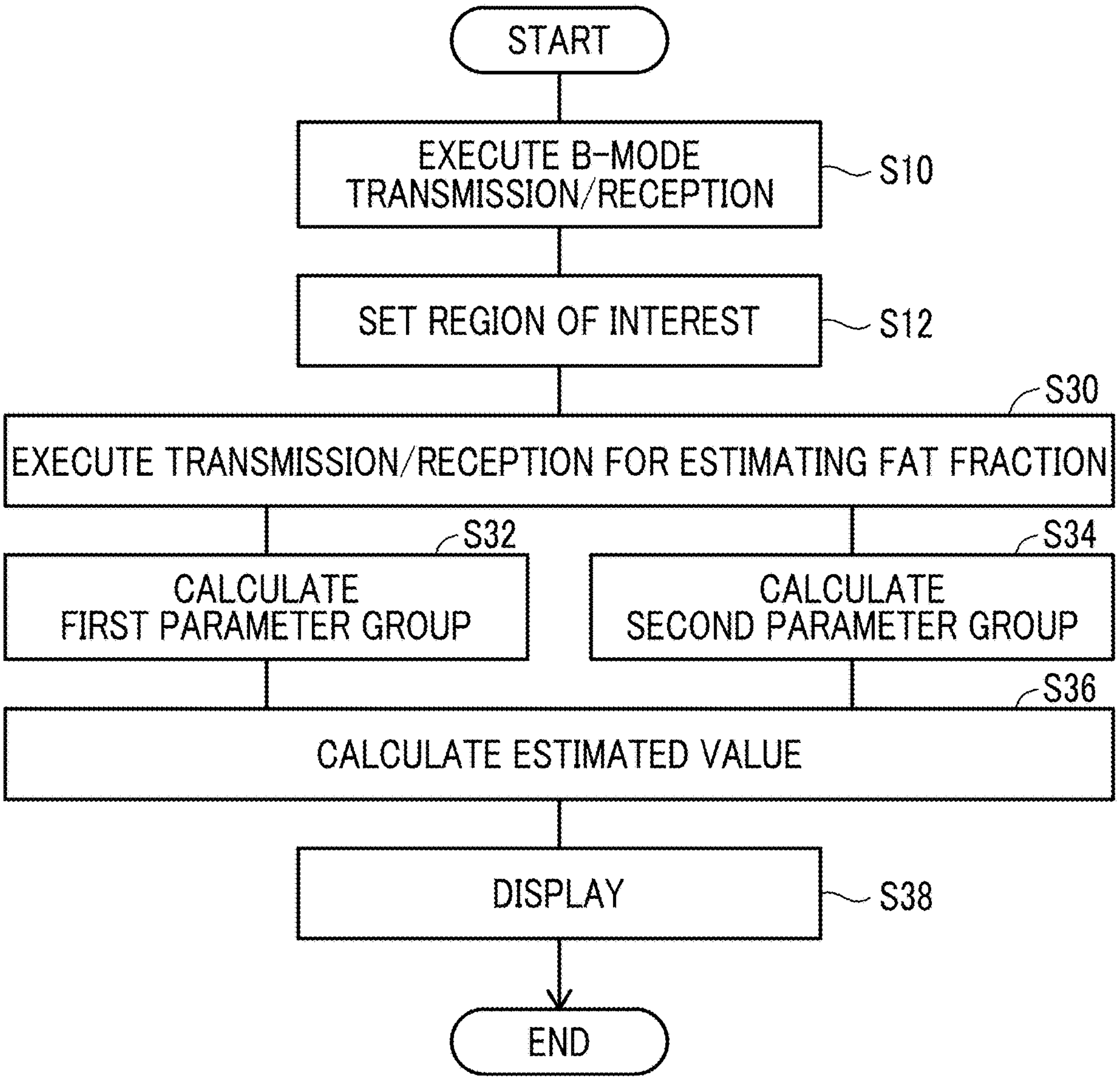
FIG. 9 is a flowchart showing an operation of the ultrasound diagnostic apparatus according to a modification example.

FIG. 9 shows an operation example of the ultrasound diagnostic apparatus according to a modification example. In S10, the B-mode transmission/reception is executed, and, in S12, the region of interest is set. In S30, transmission/reception for estimating the fat fraction is executed. For example, ultrasonic waves including a first frequency component and a second frequency component are transmitted to the region of interest, and reflected waves from the region of interest are received. As a result, the reception information is acquired.

In S32, the first frequency component included in the reception information is extracted by a first reception filter, and the first parameter group is calculated based on the first frequency component. In S34, the second frequency component included in the reception information is extracted by a second reception filter, and the second parameter group is calculated based on the second frequency component. The first reception filter has a first frequency characteristic for extracting the first frequency component, and the second reception filter has a second frequency characteristic for extracting the second frequency component. In S36, the estimated value of the fat fraction is calculated based on the parameter set including the first parameter group and the second parameter group. In S38, the estimated value is displayed.

According to this modification example, the estimated value can be obtained by one transmission/reception. In a case in which the estimation accuracy is prioritized, it is desirable to adopt the operation shown in FIG. 8.

According to the above-described embodiment, in the ultrasound diagnostic apparatus, the estimated value of the fat fraction can be calculated based on the first attenuation coefficient and the second attenuation coefficient acquired under different transmission/reception conditions. In particular, an estimated value approximating the PDFF can be calculated. Since the parameter set has a plurality of parameters other than the first attenuation coefficient and the second attenuation coefficient, the estimation accuracy of the fat fraction can be improved. Instead of or in addition to the attenuation average and the attenuation variation, other parameters obtained from the reception information may be used. The BMI may be excluded from the parameter set, or an examination value may be used instead of the BMI.

What is claimed is:

1. An ultrasound diagnostic apparatus comprising:

an ultrasound probe configured to transmit a first ultrasonic wave having a first frequency characteristic into a two-dimensional region within a liver of a subject to obtain first reception information, and to transmit a second ultrasonic wave having a second frequency characteristic different from the first frequency characteristic into the two-dimensional region to obtain second reception information; and a processor, wherein the two-dimensional region corresponds to a plurality of reception beams aligned in an electronic scanning direction, the first reception information comprises a plurality of first reception beam data obtained from the two-dimensional region, the second reception information comprises a plurality of second reception beam data obtained from the two-dimensional region, and the processor is configured to:

calculate, based on the plurality of first reception beam data, a first parameter group including a first attenuation coefficient, a first attenuation average, and a first attenuation variation;

calculate, based on the plurality of second reception beam data, a second parameter group including a second attenuation coefficient, a second attenuation average, and a second attenuation variation; and calculate an estimated value of a fat fraction based on a parameter set including the first parameter group and the second parameter group;

wherein the processor is further configured to:

generate first reference information to be compared with the first reception information and second reference information to be compared with the second reception information, calculate the first attenuation coefficient based on the first reception information and the first reference information, and calculate the second attenuation coefficient based on the second reception information and the second reference information, the first reference information is defined by a first reference intensity function, and the second reference information is defined by a second reference intensity function, the first reception information is a first reception intensity matrix P1($x$), and the second reception information is a second reception intensity matrix P2($x$), and the first reference information is a first reference intensity sequence Pref1($x$), and the second reference information is a second reference intensity sequence Pref2($x$).

2. The ultrasound diagnostic apparatus according to claim 1, wherein the processor includes a model configured to generate the estimated value that approximates a magnetic resonance imaging (MRI) proton density fat fraction (PDFF), and when the parameter set is input to the model, the estimated value is output from the model.

3. The ultrasound diagnostic apparatus according to claim 1, wherein the first frequency characteristic is a first center frequency, and the second frequency characteristic is a second center frequency different from the first center frequency.

4. The ultrasound diagnostic apparatus according to claim 1, wherein the processor is further configured to:

calculate a first attenuation matrix based on the first reception information and the first reference information, calculate the first parameter group based on the first attenuation matrix, calculate a second attenuation matrix based on the second reception information and the second reference information, and calculate the second parameter group based on the second attenuation matrix.

5. The ultrasound diagnostic apparatus according to claim 4, wherein the processor is further configured to:

calculate the first attenuation coefficient based on a specific attenuation sequence selected from the first attenuation matrix, calculate the first attenuation average and the first attenuation variation based on a plurality of attenuation sequences in the first attenuation matrix, calculate the second attenuation coefficient based on a specific attenuation sequence selected from the second attenuation matrix, and calculate the second attenuation average and the second attenuation variation based on a plurality of attenuation sequences in the second attenuation matrix.

6. The ultrasound diagnostic apparatus according to claim 1, wherein the parameter set further includes one or a plurality of parameters acquired from the subject by an examination other than an ultrasound examination.

7. The ultrasound diagnostic apparatus according to claim 1, further comprising:

an image forming unit configured to form an ultrasound image based on reception information different from the first and second reception information; and a display device configured to display the ultrasound image, at least one of the first and second attenuation coefficients, and the estimated value of the fat fraction.

* * * * *